United States Patent [19]

Cornils et al.

[11] 4,435,603
[45] Mar. 6, 1984

[54] METHOD FOR PREVENTING CAKING OF POLYOLS

[75] Inventors: Boy Cornils, Dinslaken; Hanswilhelm Bach, Duisburg; Roderich Gärtner, Dinslaken; Wilhelm Gick, Duisburg, all of Fed. Rep. of Germany

[73] Assignee: Ruhrchemie Aktiengesellschaft, Oberhausen, Fed. Rep. of Germany

[21] Appl. No.: 242,772

[22] Filed: Mar. 11, 1981

[30] Foreign Application Priority Data

Mar. 15, 1980 [DE] Fed. Rep. of Germany ....... 3010138

[51] Int. Cl.³ .................... C07C 27/26; C07C 29/94
[52] U.S. Cl. .................................. 568/701; 568/704; 568/852; 568/853
[58] Field of Search ................ 568/701, 704, 852, 853

[56] References Cited

U.S. PATENT DOCUMENTS

| 1,754,457 | 4/1930 | Calcotts et al. | 568/701 |
|---|---|---|---|
| 2,441,795 | 5/1948 | Sexton et al. | 568/701 |
| 2,441,849 | 5/1948 | Sexton | 568/701 |
| 2,822,409 | 2/1958 | Gwynn et al. | 568/701 |
| 2,846,477 | 8/1958 | Leach et al. | 568/701 |
| 3,163,680 | 12/1964 | Audouze et al. | 568/853 |
| 3,439,050 | 4/1969 | McKeever et al. | 568/701 |
| 3,623,984 | 11/1971 | Carlos | 568/701 |
| 3,808,280 | 4/1974 | Merger et al. | 568/853 |
| 3,920,760 | 11/1975 | Heinz | 568/853 |

OTHER PUBLICATIONS

Uede et al., "Chem. Abstract", vol. 83, 11126k (1975).

Primary Examiner—Werren B. Lone
Attorney, Agent, or Firm—Sprung, Horn, Kramer & Woods

[57] ABSTRACT

A polyol composition comprising a solid polyol which is crystalline under normal conditions and, as an anticaking agent therefor, a tertiary amine containing at least two identical organic substituents, each having two to twenty carbon atoms. A method of preventing caking of polyols is disclosed wherein to such polyols there is added at least one of such tertiary amines, preferably in a concentration of 0.05 to 0.25 percent by weight based on the weight of the polyol.

17 Claims, No Drawings

METHOD FOR PREVENTING CAKING OF POLYOLS

BACKGROUND OF THE INVENTION

1. Field of the Invention

This invention relates to a polyol composition comprising a solid polyol which is crystalline under normal conditions and a tertiary amine containing at least two identical organic substituents, each of which has two to twenty carbon atoms. More especially, this invention relates to the prevention of caking of solid polyols and the improvement in the storability of such solid polyols under normal conditions, especially under conditions where the polyols are subjected to high pressures.

2. Discussion of Prior Art

Polyols are important intermediates for chemical synthesis, which in some cases have achieved industrial importance and are used, inter alia, for producing plastics such as polyurethanes, polycarbonates, alkyd resins, lubricants, plasticizers, lacquers and varnishes. The generally easy accessibility of polyols is a decisive factor in their wide range of uses.

Examples of technically employed polyols are 2,2-dimethyl-1,3-propanediol (neopentyl glycol), 1,6-hexanediol and trimethylolpropane. Such polyols are prepared by catalytic hydrogenation of the corresponding carboxylic acids or esters, as in the case of 1,6-hexanediol, or mixed aldolization of aldehydes with formaldehyde and subsequent reduction of the hydroxyaldehydes, such as in the case of 2,2-dimethyl-1,3-propanediol or trimethylolpropane.

In order to ensure ease of handling during further processing, the polyols are suitably formulated and are commercially available, for example, in the form of flakes, tablets or briquettes.

The caking tendency of polyols is found to be extremely troublesome during storage. The cause of this is not always known. In the case of 2,2-dimethyl-1,3-propanediol it was found that in the solid state it exists in two different modifications, which are reversibly convertible into one another. The transformation temperatures of the thermodynamically unstable modification to the thermodynamically stable form, and vice versa, are 42° C. and 33° C. respectively, with supercooling. The heat of transformation of the two modifications has been calculated as 13.7 kJ/mole (H. P. Frank, K. Krzenicki, H. Völlenkle, Chemiker-Ztg. 97, 206, (1973)) and is approximately three times as great as the heat of fusion. On account of these physical properties of 2,2-dimethyl-1,3-propanediol, the production of the pure product in the form of flakes is not without problems. Difficulties arise, especially in the case of extra high quality products, which are due to the fact that the material being formulated is not completely transformed, e.g. on the flake-forming roller, into the thermodynamically more stable "low temperature modification". As a result, the neopentyl glycol subsequently changes into the corresponding "low temperature modification" in the drums and barrels for commercial sale, and the very high heat of transformation is liberated. The heat of transformation thus produces a considerable temperature rise in the product for sale and results in a more or less pronounced caking of the flaking product. In extreme cases the flow properties of the product are considerably impaired.

In order to avoid the aforementioned complications, Japanese Patent Specification 74 88 813 (CA 83, 11126 K (1975)) describes the addition of esters of organic acids or of acetals as anti-caking agents. Thus, neopentyl glycol to which 0.005% by weight of cellulose acetate butyl ester has been added, and which after formulation has been subjected for more than 30 days to a pressure of 230 p/cm$^2$, does not exhibit any caking.

Since the described additives largely lose their effectiveness when fairly high pressures are reached, such as are produced on storage in the nowadays conventional form of fairly high stacks of sacks and bags, and moreover cause difficulties during the further processing, e.g. to form alkyd resins, polymers, lubricants and additives, the objective therefore arose of avoiding the described disadvantages and of discovering anticaking agents that are effective also under unfavorable conditions.

SUMMARY OF THE INVENTION

Broadly, this invention contemplates a polyol composition comprising a polyol which is crystalline under normal conditions and a tertiary amine containing at least two identical organic substituents, each having two to twenty carbon atoms.

This invention particularly contemplates the prevention of caking of polyols which are crystalline under normal conditions by adding thereto such tertiary amine, especially in a concentration of 0.05 to 0.25 percent by weight of amine, based upon the weight of the polyols.

Preferably, the tertiary amines employed are those whose organic substituents contain two to twelve carbon atoms, per substituent.

The substituents of the tertiary amine can be straight, chain, or branched organic radical which can be unsubstituted or singly or multiply substituted. These radicals can be alicyclic, araliphatic or aromatic radicals. In particular, the following radicals are contemplated: alkyl, cycloalkyl, aryl, especially phenyl, aralkyl, and alkanol. In addition, the nitrogen atom of the tertiary amine can be part of a cyclic structure. Thus tertiary heterocyclic amines are also contemplated. In such instance, the compounds are considered to have two identical organic substituents since two of the three bonds of the nitrogen atom are connected to the same organo substituent.

Examples of amines which are particularly contemplated are: tri-n-hexylamine, tri-n-octylamine, triisooctylamine, triisononyl-amine, triphenylamine, tricyclohexylamine, N,N-diphenylbenzylamine, pyridine, 3-methylpyridine, N-phenylpiperidine, N,N-dimethylethanolamine and triethanolamine.

In addition to pure means, mixtures of two or more amines, each depending on the boiling point range of the molten polyol, may also be added before purification distillation or before formulation, i.e., before shaping and forming e.g. by flake formation.

The amine or amine mixtures are preferably employed in a concentration of 0.005 to 0.25 percent by weight of amine or amine mixture based upon the weight of the polyol, more preferably 0.02 to 0.15 percent by weight of amine or amine mixture, based upon the weight of polyol.

The amine or amine mixture can be added to the polyol while the same is in molten form. Alternatively, the amine or amine mixture can be added to the polyol after the same has assume the solid state. Preferably, the amine anti-caking agent is intermixed with the polyol as homogeneously as possible. This can be effected by the use of known mixing devices, metering pumps and the like.

In order to more fully illustrate the nature of the invention and manner of practicing the same, the following examples are presented.

Molten polyol (diol) is poured into a heated stirred container (volume 600 l) and the anti-caking agent is added via a suitably dimensioned metering device, which is likewise heated. The molten polyol is homogenized by stirring. Alternatively, a concentrate consisting of molten polyol and the necessary amount of anti-caking agent for the whole amount of polyol can be placed in the metering device, while stirring, and then added to the stirred container.

Following this the molten polyol to which the anti-caking agent has been added is fed to a cooled flake-forming roller (hourly output: 20 kg/hour). The flakes thereby formed are examined as regards their storage suitability.

The table gives the results of some experimental examples. In all the cases described the flakes thus produced did not exhibit any caking properties at all, whereas the flakes produced in the comparison experiments without the addition of anti-caking agent (addition of amine) no longer exhibited satisfactory flow properties after short-term storage, as a result of agglomeration, lump formation and caking.

EXPERIMENTAL EXAMPLES

| Diol | Purity | Amine | Amine concentration, % by wt. | Flow properties of the flakes |
|---|---|---|---|---|
| Neopentyl glycol | 99.8 | Triisononylamine | 0.02 | good |
| Neopentyl glycol | 99.8 | Triphenylamine | 0.1 | good |
| Neopentyl glycol | 99.8 | Triisooctylamine Triphenylamine (1:1) | 0.1 | good |
| 2-methyl-2-n-propyl-propane-1.3-diol | 99.7 | N,N—dimethyl-ethanolamine | 0.05 | good |
| 2-ethyl-2-n-butyl-propane-1.3-diol | 99.8 | Triethanolamine | 0.15 | good |

What is claimed is:

1. A polyol composition consisting essentially of a solid polyol which is crystalline under normal conditions and a tertiary amine containing at least two identical organic substituents, each having 2 to 20 carbon atoms, said tertiary amine being present in said polyol composition in a concentration of 0.005 to 0.25 percent by weight, based upon the weight of said polyol.

2. A composition according to claim 1, wherein each substituent of said tertiary amine contains two to 12 carbon atoms.

3. A composition according to claim 1, wherein said organic substituents are straight chain or branched aliphatic, substituted or unsubstituted alicyclic, araliphatic or aromatic substituents.

4. A composition according to claim 1, wherein said tertiary amine is a heterocyclic tertiary amine containing a nitrogen in the ring structure and said ring contains 4 to 8 carbon atoms, is saturated or singly or multiply unsaturated and is unsubstituted or C-alkylated or N-alkylated.

5. A composition according to claim 1, comprising at least two of said tertiary amines.

6. A composition according to claim 5, wherein said tertiary amines are present in equal proportions.

7. A method for preventing caking of a polyol which is crystalline under normal condition which comprises contacting the same with a tertiary amine containing amine containing at least two identical organic substituents each having two to 20 carbon atoms.

8. A method according to claim 7, wherein said organic substituents each contain two to 12 carbon atoms.

9. A method according to claim 7, wherein 0.05 to 0.25 percent by weight of amine or mixture of tertiary amine is added to said polyol, said amount being based upon the weight of said polyol.

10. A method according to claim 9, wherein the organic substituents are straight chain or branched aliphatic, substituted or unsubstituted alicyclic, aliphatic, or aromatic substituents.

11. A method according to claim 9, wherein said tertiary amine is a heterocyclic nitrogen compound whose ring is saturated or is singly or multiply unsaturated, contains 4 to 8 carbon atoms and is unsubstituted or is C-alkylated or N-alkylated.

12. A method according to claim 9, wherein two or more tertiary amines are added to the polyol.

13. A method according to claim 9, wherein said amine or a mixture of said amines is added to said polyol before purification distillation thereof or before formulating the polyol into a final solid form.

14. A method according to claim 9, wherein said amine is tri-n-hexylamine, tri-n-octylamine, triisooctylamine, triisononyl-amine, triphenylamine, tricyclohexylamine, N,N-diphenylbenzylamine, pyridine, 3-methylpyridine, N-phenylpiperidine, N,N-dimethylethanolamine or triethanolamine.

15. A polyol composition according to claim 1, wherein said amine is tri-n-hexylamine, tri-n-octylamine, triisooctylamine, triisononyl-amine, triphenylamine, tricyclohexylamine, N,N-diphenyl-benzylamine, pyridine, 3-methylpyridine, N-phenylpiperidine, N,N-dimethylethanolamine or triethanolamine.

16. A polyol composition according to claim 1 wherein said polyol is selected from the group consisting of 2,2-dimethyl-1,3-propanediol, 1,6-hexanediol and trimethylolpropane.

17. A method according to claim 9 wherein said polyol is selected from the group consisting of 2,2-dimethyl-1,3-propanediol, 1,6-hexanediol and trimethylolpropane.

* * * * *